(12) United States Patent
Kawai (10) Patent No.: US 7,442,150 B2
(45) Date of Patent: Oct. 28, 2008

(54) LEG STRENGTH MEASURING APPARATUS

(75) Inventor: Shigehiro Kawai, Tajimi (JP)

(73) Assignee: Japana Co., Ltd., Nagoya (JP)

( * ) Notice: Subject to any disclaimer, the term of this patent is extended or adjusted under 35 U.S.C. 154(b) by 0 days.

(21) Appl. No.: 11/380,190

(22) Filed: Apr. 25, 2006

(65) Prior Publication Data

US 2006/0179938 A1 Aug. 17, 2006

(51) Int. Cl.
*A63B 71/00* (2006.01)
(52) U.S. Cl. .................. 482/8; 482/1; 482/9; 434/247; 601/23
(58) Field of Classification Search ........... 482/1–9, 482/900–902; 434/247; 702/127, 138, 101, 702/139, 129, 173, 182; 73/379.01; 601/23, 601/33–35
See application file for complete search history.

(56) References Cited

U.S. PATENT DOCUMENTS

| | | | |
|---|---|---|---|
| 3,805,603 A | 4/1974 | Ettlinger | |
| 4,164,875 A | 8/1979 | Kantar | |
| 4,906,192 A | 3/1990 | Smithard | |
| 5,049,079 A | 9/1991 | Furtado | |
| 5,690,591 A | 11/1997 | Kenmochi | |
| 5,813,864 A | 9/1998 | Ikuta | |
| 5,878,378 A * | 3/1999 | Brommer et al. ............ | 702/139 |
| 6,139,473 A | 10/2000 | Koyama | |
| 6,270,403 B1 | 8/2001 | Watanabe | |
| 6,539,336 B1 * | 3/2003 | Vock et al. .................. | 702/182 |
| 6,582,300 B2 | 6/2003 | Watanabe | |
| 6,589,630 B1 * | 7/2003 | Crow .......................... | 428/167 |
| 6,884,214 B2 * | 4/2005 | Itagaki ........................ | 600/300 |
| 7,260,545 B1 | 8/2007 | Schaer | |
| 2003/0017883 A1 | 1/2003 | Yoshiike | |

FOREIGN PATENT DOCUMENTS

| | | |
|---|---|---|
| JP | H01-90585 U | 6/1989 |
| JP | H03-212263 A | 9/1991 |
| JP | H05-33032 U | 4/1993 |
| JP | H07-213745 A | 8/1995 |
| JP | H08-131594 A | 5/1996 |
| JP | H09-149957 A | 6/1997 |
| JP | H09-224922 A | 9/1997 |
| JP | H10-085453 A | 4/1998 |
| JP | H11-156047 A | 6/1999 |
| JP | 2002-048630 A | 2/2002 |
| JP | 2002-065652 A | 3/2002 |
| JP | 2002-136632 A | 5/2002 |
| JP | 2002-312371 A | 10/2002 |
| JP | 2002-346015 A | 12/2002 |
| JP | 2003-199728 A | 7/2003 |
| JP | 2003-240630 A | 8/2003 |
| WO | WO98/10847 | 3/1998 |

\* cited by examiner

*Primary Examiner*—Glenn Richman
(74) *Attorney, Agent, or Firm*—Hiroe & Associates; Michael L. Crapenhoft (57) ABSTRACT

A leg strength measuring apparatus is capable of measuring a gravity center distribution of loads and leg strength which can in turn serve as a reference for the selection of a ski, a snowboard, ski boots, or snowboarding boots appropriate for a user of the apparatus. The leg strength measuring apparatus includes two footplates upon which a person to be measured steps separately with his left and right feet, and load sensors for detecting loads applied to each of the footplates at least at three points.

7 Claims, 9 Drawing Sheets

| | | |
|---|---|---|
| YOUR NAME | LAST NAME [ ] | FIRST NAME [ ] |
| PHONETIC SPELLING | LAST NAME [ ] | FIRST NAME [ ] |

ADDRESS [ ]

TEL [ ] – [ ] – [ ]

FAX [ ] – [ ] – [ ]

E-mail [ ]

BIRTHDAY [ ] YEAR [ ] MONTH [ ] DAY

GENDER   MALE ○   FEMALE ○

HEIGHT [ ] cm

FOOT SIZE [ ] cm

QUALIFICATION [ FIRST GRADE ▽ ]

USUAL SKIING AREA [ ▽ ]

NUMBER OF SKIING DAYS A YEAR [ 30 DAYS ]

CURRENT USE GOODS

SKI BOARD [ ▽ ]

BOOTS [ ▽ ]

BINDING [ ▽ ]

| | |
|---|---|
| YOUR NAME | ○○ |
| PHONETIC SPELLING | ○○ |
| GENDER | MALE |
| HEIGHT | 183cm |
| FOOTSIZE | 28cm |
| QUALIFICATION | FIRST GRADE |
| WEIGHT | 75kg |
| LEG STRENGTH | 145kg |
| AC (LEG STRENGTH/WEIGHT) | 1.93 |
| MAXIMUM LOAD | 220kg |
| SKILL LEVEL | AB |

AC REFERENCE DATA

| | LEG STRENGTH LARGE | LEG STRENGTH MIDDLE | LEG STRENGTH SMALL |
|---|---|---|---|
| MALE | | | |
| FEMALE | | | |

Fig.8

LEG STRENGTH MEASURING APPARATUS

BACKGROUND OF THE INVENTION

The invention relates to sports equipment and apparatus for measuring a user's physical characteristics and selecting and adjusting sports equipment to suit that user. More particularly, the invention provides apparatus for measuring a user's weight, weight distribution, and leg strength, and then assisting in the selection and adjustment of snow skis or snowboards with characteristics suitable for that particular user.

For a skier or a snowboarder, it is desirable to know a distribution of load points applied to the sole of his boot, the person's leg strength, etc., in selecting a ski, a snowboard, and ski or snowboard boots suitable for that user.

A leg strength measuring apparatus is disclosed in Japanese Published Patent Application No. 2002-65652. That leg strength measuring apparatus includes a seat, a footplate provided at a front side of the seat, and a load sensor for measuring a load applied to the footplate. A person whose leg strength is to be measured steps on the footplate while seated in the seat. The resulting force is measured with the load sensor, thereby enabling the leg strength of the person to be measured.

The leg strength required for skiing or snowboarding is the leg strength applied while bending the knees from a standing posture (i.e., while flexing and extending the knees). The leg strength measuring apparatus of the published Japanese application, however, measures leg strength with the person seated in the seat, in a posture completely different from the posture used in actually skiing or snowboarding. It is therefore impossible to accurately measure the leg strength used in skiing or snowboarding with the leg strength measuring apparatus of the published application. For this reason, the leg strength measured by the leg strength measuring apparatus of described in that application can not serve as an accurate reference for selecting a ski, a snowboard, boots for skiing or snowboarding, etc.

The present invention therefore has been made in consideration of the foregoing actual conditions in which such equipment is used, and its object is to provide a leg strength measuring apparatus capable of measuring distributions of load points and leg strength that can serve as an appropriate reference for selecting and adjusting equipment suitable for use by that particular person.

SUMMARY OF THE INVENTION

One embodiment of leg strength measuring apparatus according to the invention includes two footplates onto which a person whose leg strength is to measured steps separately with his left and right feet, and a load sensor for detecting loads applied to each footplate at least at three points.

An embodiment that is arranged to include two footplates for a user's left and right feet and to measure loads applied to each footplate at least at three points makes it possible to analyze the weight of the person to be measured and the state of the planar distribution of the loads applied when the user flexes and extends his knees, based upon the values measured at the three points.

The apparatus may include two footplates onto which the person steps separately with his left and right feet, and a load sensor operable to detect a vertical load applied to each footplate and a moment associated therewith.

Such an apparatus makes it possible to analyze the weight of the person and the state of the plane distribution of the loads when flexing and extending knees with only a single load sensor in each footplate.

The apparatus may include leg strength calculation apparatus operable to calculate the leg strength of the person by subtracting the measured weight of the person from a maximum load that is detected by the load sensor while the person stands on the footplates and flexes and extends his legs.

Such apparatus makes it possible to obtain the leg strength of the person by subtracting the weight from the load applied while the person flexes and extends his knees.

The apparatus may include storage means operable to store the maximum load and the weight of the person based upon an output of the load sensor.

Such apparatus makes it possible to obtain the maximum load applied when the person flexes and extends his knees and the leg strength of the person, based upon measured values stored in the storage means.

The apparatus may include positioning or gap adjusting means for adjusting a separation gap between the two footplates.

Such apparatus enables a separation width between the two footplates to be adjusted to a width suitable for the person as needed.

The apparatus may include a handrail.

Such apparatus makes it possible to ensure the safety of the person because the handrail is provided.

The apparatus may include a handrail that moves together with one of the footplates.

Such apparatus allows the person to mount the footplate while grasping the handrail.

The apparatus may include a boot fixing section configured for the fixation of ski or snowboard boots.

Such apparatus allows the person to be positioned on the footplate with ski or snowboard boots on.

The apparatus may include a load sensor that is capable of continuously or sequentially detecting a plurality of momentary values applied during the users bending and stretching movements.

Such apparatus makes it possible to detect the conditions of the person's weight shifts during bending and stretching movements.

The apparatus may include analyzing means for analyzing a planar distribution of the loads based upon output values from the load sensor.

Such apparatus makes it possible to analyze the planar distribution of the weight of the person.

The footplates may have a shape that allows a ski or a snowboard to be mounted on them.

Such apparatus enables the person to position himself on the footplate while wearing skis or a snowboard.

The footplate may be formed of a rigid member that is difficult to deform.

Such apparatus enables the load applied to the footplate to be efficiently transmitted to the load sensor because the footplate is difficult to deform.

The apparatus may include a footplate that can be fixed in a position that is inclined in a front-to-back or a transverse direction.

Such apparatus makes it possible to measure the leg strength etc. of the person by inclining the footplate in a posture close to the situation in which the person is actually skiing or snowboarding.

BRIEF DESCRIPTION OF THE FIGURES

The invention will be best understood by reference to the following detailed description, taken in conjunction with the appended drawings, in which.

DETAILED DESCRIPTION OF PREFERRED EMBODIMENTS

Figure 1:
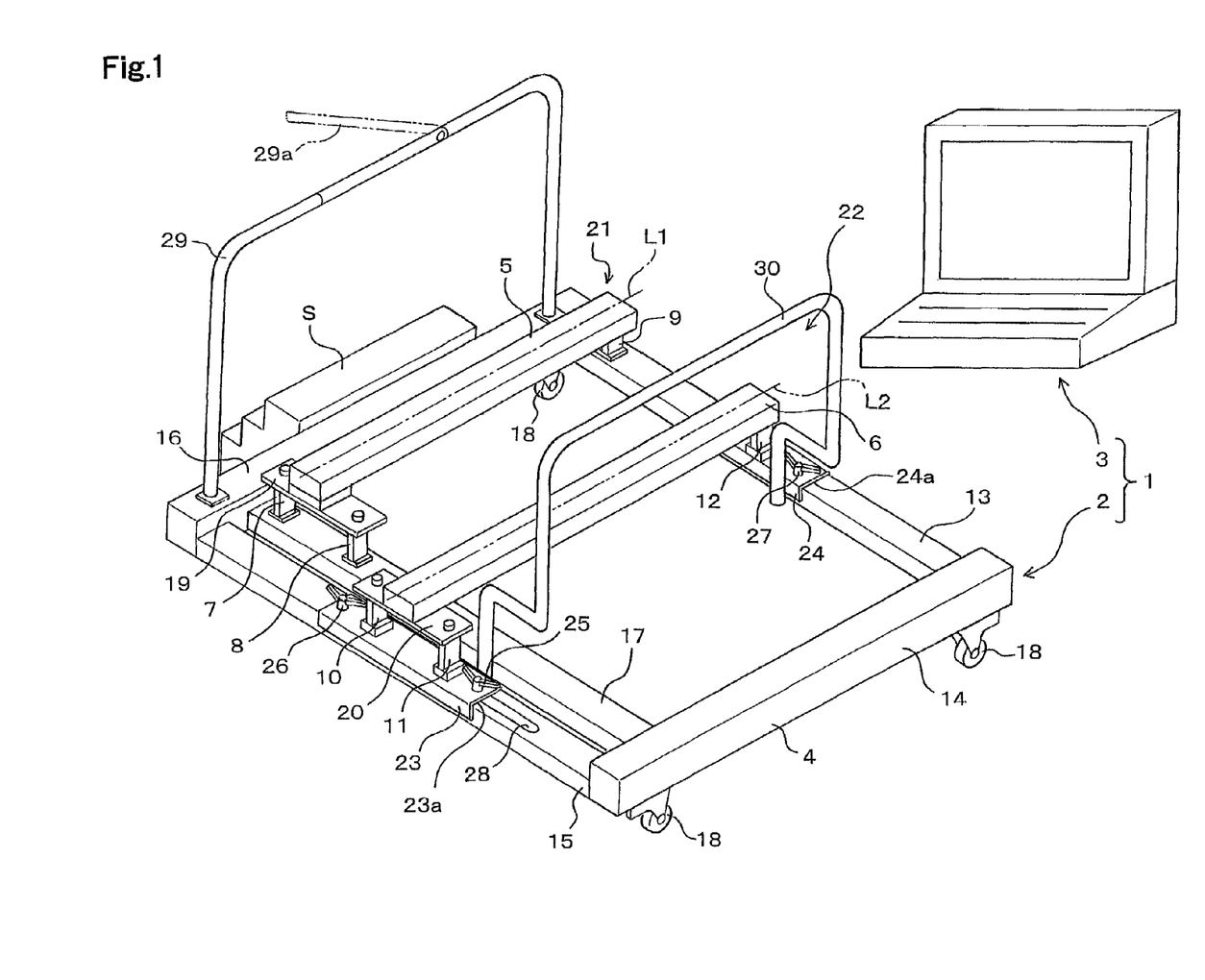
FIG. 1 is a perspective view of a leg strength measuring apparatus that embodies the invention.

As shown in FIG. 1, a leg strength measuring apparatus 1 includes a measurer 2 and a personal computer (hereinafter referred to as a PC) 3. The measurer 2 is an appliance for measuring a load such as the weight of the person to be measured. The PC 3 is for inputting the values measured by the measurer 2 and for executing a process for calculating the leg strength of the person, the plane distribution of the load, etc. The measurer 2 includes a base stand 4, and two footplates 5 and 6 provided on the base stand 4 in parallel to one another. The footplates 5 and 6 are provided as separate elements so that the person whose leg strength is measured steps on them individually with his left and right feet. Three load sensors (load cells) 7, 8, and 9 are located between one footplate 5 and the base stand 4, with another three load sensors 10, 11, and 12 located between the other footplate 6 and the base stand 4. Each of the sensors 7 to 12 detects a vertical load applied to one of the footplates 5 and 6. In this description, a "vertical" load is load in the vertical direction applied to one or the other of the footplates 5 and 6.

The base stand 4 may be formed into any desired shape so long as it is of a shape that allows the footplates 5 and 6 to be supported. It may, for example, be formed with a four-cornered framework that includes four supporting bodies 13, 14, 15 and 16 assembled in a square configuration, and may include an auxiliary body 17 assembled in parallel to the supporting body 15. Providing casters 18 at the four corners of the base stand 4, moreover, allows the base stand 4 to be made movable and positioned in different desired locations. Where the base stand 4 is formed in such a manner, one footplate 5 can be constructed as a span between the supporting body 13 and the auxiliary body 17, with the other footplate 6 constructed as a span between the supporting body 13 and the supporting body 15.

The footplates 5 and 6 may be formed into a shape that is long and narrow. Both of the footplates 5 and 6 are preferably formed of as rigid members that are not susceptible to deformations such as bending and deflection, so that the loads applied to the footplates 5 and 6 themselves are transmitted efficiently to the load sensors 7 to 12. A sensor fitting section 19 that is wider in width than the footplate 5 is fixed to the underside of one end of one footplate 5, with load sensors 7 and 8 positioned beneath the sensor fitting section 19. The additional load sensor 9 is provided on the underside of the opposite end of the footplate 5.

Another sensor fitting section 20 that is wider than the footplate 6 is fixed to the underside at one end of that footplate 6. Corresponding load sensors 10 and 11 are provided on the underside of the sensor fitting section 20, with another load sensor 12 located at the underside at the other end of the footplate 6.

Figure 2:
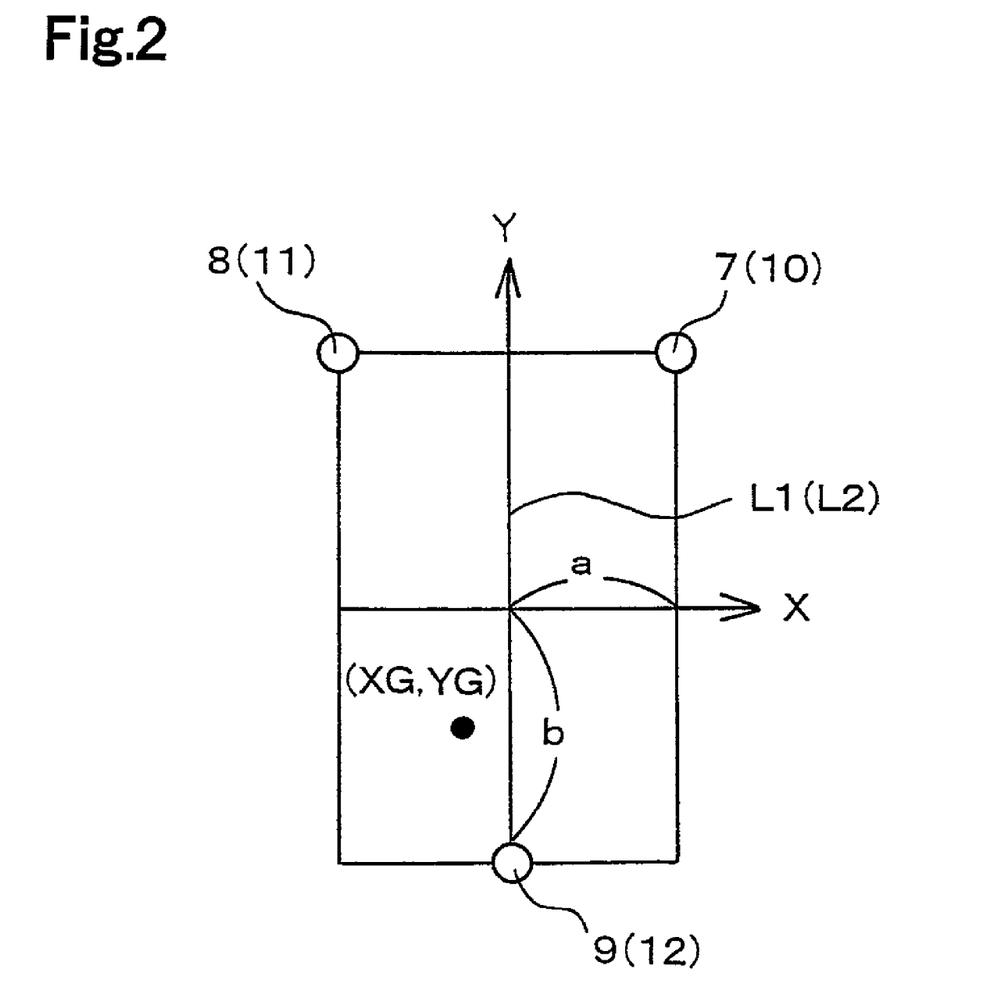
FIG. 2 is a schematic view illustrating a positional relationship between load sensors used in the apparatus of FIG. 1.

The assembly comprising the sensor fitting section 19, the three load sensors 7 to 9, and the first footplate 5 forms one footplate unit 21. The sensor fitting section 20 and the other three load sensors 10 to 12 on the other footplate 6 comprises a second footplate unit 22. As FIGS. 1 and 2 illustrate, the load sensor 9 is positioned on an axial line L1 of one footplate 5, and the load sensors 7 and 8 are placed at positions that form an isosceles triangle in combination with the load sensor 9. The load sensor 12, on the other hand, is positioned on an axial line L2 of the other footplate 6, with the load sensors 10 and 11 at positions that form an isosceles triangle in relation to the load sensor 12.

One footplate unit 21, arranged as described above, is constructed as a span between the supporting body 13 and the auxiliary body 17. The footplate unit 21 is fixed to the auxiliary body 17 and the supporting body 13 with the two load sensors 7 and 8 of the footplate unit 21 interposed between the sensor fitting section 19 and the auxiliary body 17 and with the load sensor 7 interposed between the footplate 5 and the supporting body 13.

Where the other footplate unit 22 is constructed as a span between the supporting body 13 and the supporting body 15, that footplate unit 22 can be made movable along the supporting body 13 and supporting body 15. In this embodiment, moving bodies 23 and 24 are movable along the supporting bodies 13 and 15 with the tip and the rear end of the second footplate unit 22 mounted to these two moving bodies 23 and 24. This configuration allows the second footplate unit 22 to be moved toward and away from the first footplate unit 21 along the longitudinal direction of the two supporting bodies 13 and 15, thereby making it possible to arbitrarily adjust the separation gap between the two footplate units 21 and 22.

In particular, and as FIG. 1 illustrates, the moving bodies 23 and 24 may be formed, for example, with a downward-facing, roughly C-shaped cross-section. The moving body 23 may be fitted onto the supporting body 15 in such a manner that an opening 23a side of the moving body 23 fits over the supporting body 15. The other moving body 24 may be fitted onto the supporting body 13 in such a manner that an opening 24a side of the moving body 24 fits over the supporting body 13. In that way, the moving bodies 23 and 24 are fitted onto the two supporting bodies 13 and 15 and movable along the longitudinal direction of the supporting bodies 13 and 15. The tip side of the footplate unit 22 is mounted on the moving body 23 in such a manner that the two load sensors 10 and 11 are interposed between the sensor fitting section 20 and the moving body 23, and the rear end side of the footplate unit 22 is mounted on the moving body 24 so that the load sensor 12 is interposed between the footplate 6 and the moving body 24.

To facilitate the positioning of the moving bodies 23 and 24 for the supporting bodies 13 and 15, the moving bodies 23 and 24 are bored to receive screws 25, 26 and 27, with elongate holes 28 provided in the supporting bodies 13 and 15 along the length of the supporting bodies. The screws 25, 26 and 27 and nuts (not shown in the figure) can be tightened in the elongate holes 28, in an arrangement in which the moving bodies 23 and 24 can be positioned and adjusted as desired on the supporting bodies 13 and 15.

A gap adjusting mechanism, which allows for adjustment of the separation gap between the footplates 5 and 6, is thereby formed by the moving bodies 23 and 24, acting in cooperation with the screws 25, 26 and 27.

All of the load sensors 7 to 12 provided in both of the footplate units 21 and 22 are set so that the loads applied to the footplates 5 and 6 are measured at an identical sampling interval.

In addition, one handrail 29 is fixed to the supporting body 16, with opposite ends of another handrail 30 fixed to the moving bodies 23 and 24, thereby enabling the second handrail 30 to move together with the movable footplate unit 22 and the moving bodies 23 and 24. Providing a grip made of rubber, etc., on each of the handrails 29 and 30 allows easy gripping. Furthermore, as suggested by the phantom line in FIG. 1, an opener/closer 29a may be provided in one portion of the handrail 29 on the fixed side to allow the person to pass through, and in addition thereto, a step S may be provided to allow the person conveniently to mount the footplates 5 and 6.

Figure 3:
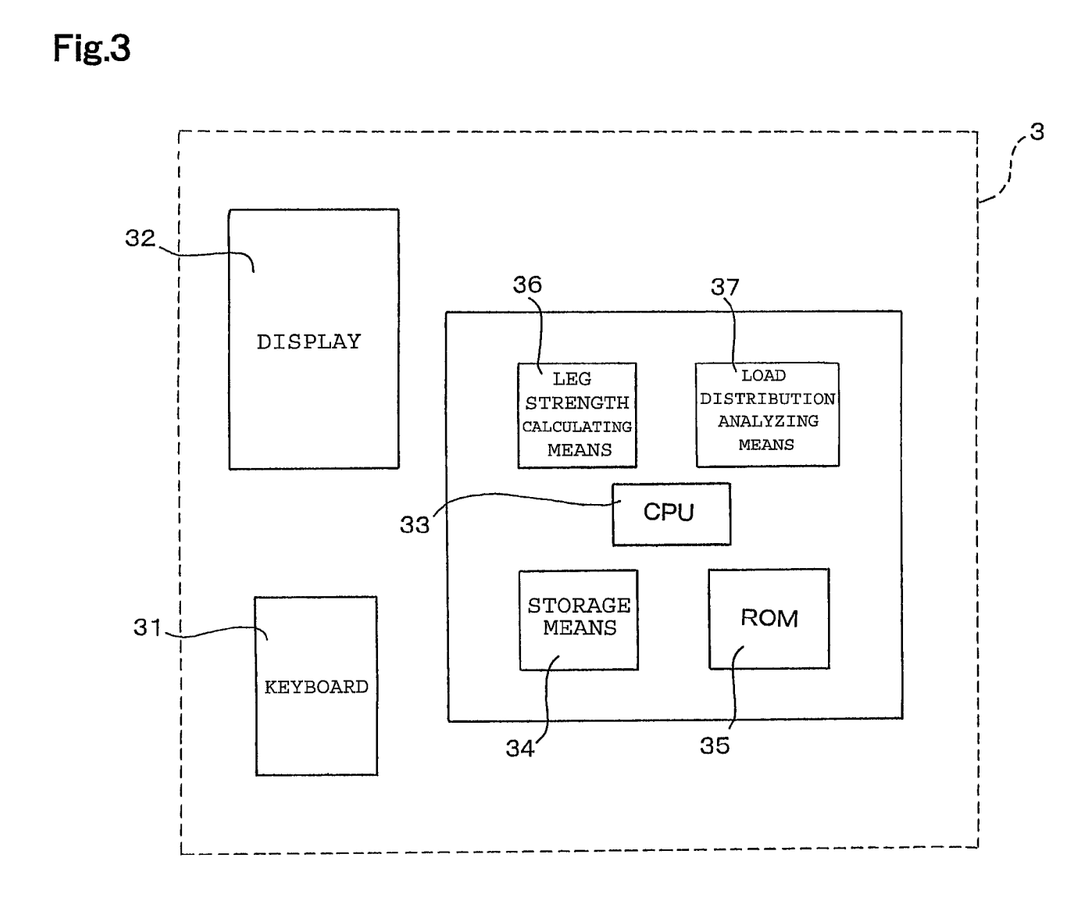
FIG. 3 is a block diagram illustrating schematically elements of an embodiment of apparatus according to the invention.

As shown in FIG. 3, the PC 3 includes a keyboard as an input means 31, a display as a display means 32, a CPU 33, a RAM as a storage means 34, a ROM 35, a leg strength calculating means 36, and a load distribution analyzing means 37.

Figure 4:
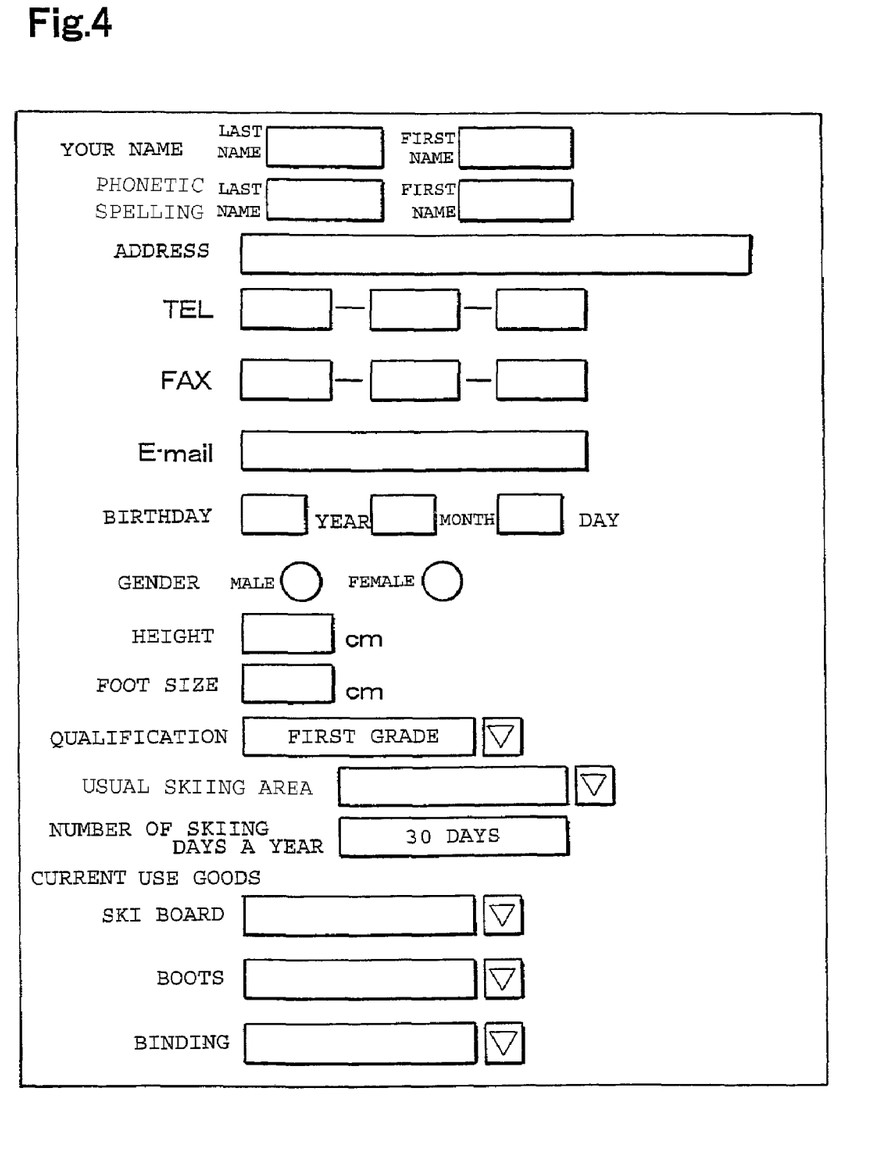
FIG. 4 is a front view of an input device and an illustration of a screen into which information for a person whose physical characteristics are to be measured is input.

The input means 31 is for the entry of information such as the name of the person being measured. The input means 31 may be, for example, a touch-panel, a keyboard, etc., for entering information, and as shown in FIG. 4, various kinds of information concerning the person such as a name, an address, and a birthday may be entered.

Figure 5:
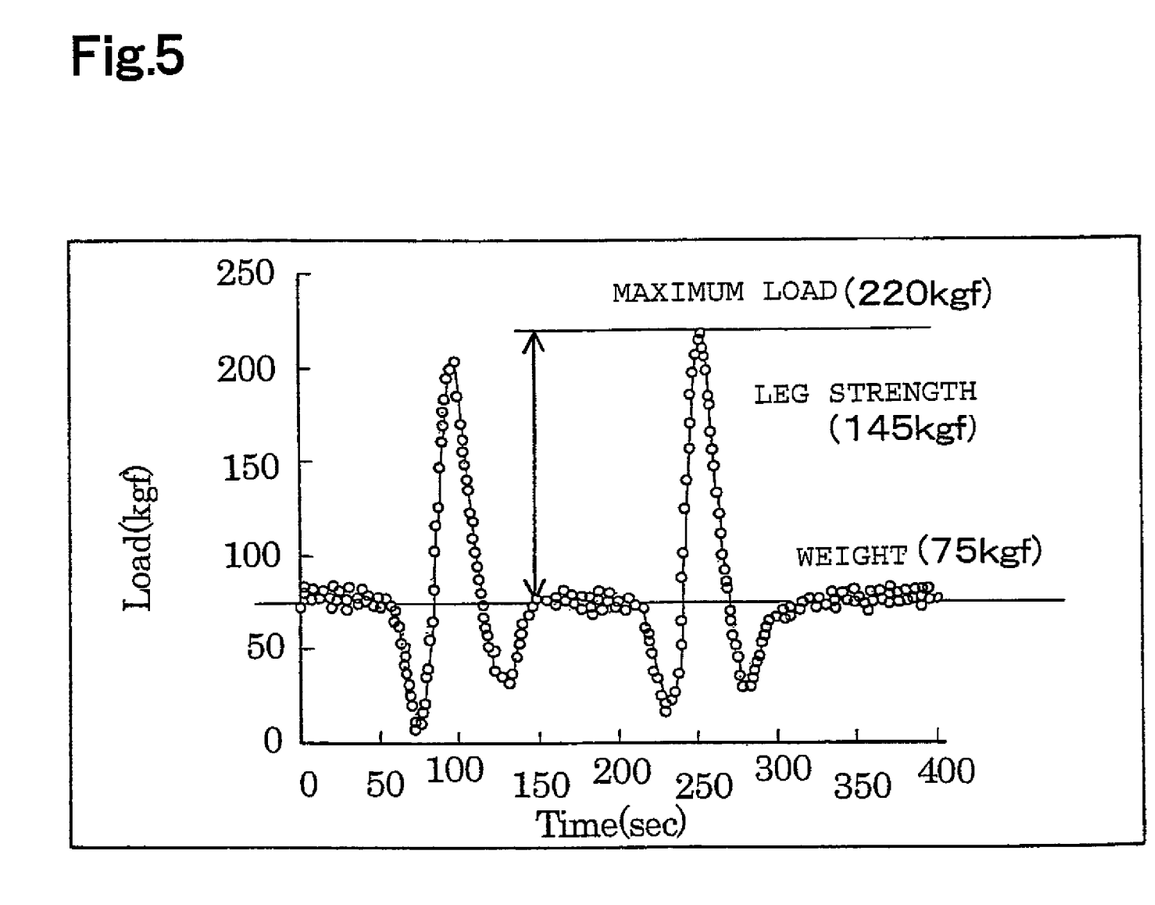
FIG. 5 is a graph display illustrating values measured by the apparatus.

The storage means 34 operates to store a series of values measured by the load sensors 7 to 12. That is, in the case where the person has mounted the footplates 5 and 6 to flex and extend his legs twice by way of experiment, the values measured in the measuring device 2 fluctuate as shown in FIG. 5. The storage means 34 stores the series of the measured values.

The leg strength calculating means 36 calculates the leg strength of the person. As FIG. 5 indicates, by subtracting the weight of the person from the load exerted by the person during bending and stretching, i.e., the load maximums, the leg strength of the person can be calculated. In the example shown in FIG. 5, the maximum load is 220 kgf and the weight is 75 kgf, whereby the leg strength of the person is calculated as 145 kgf.

Figure 6:
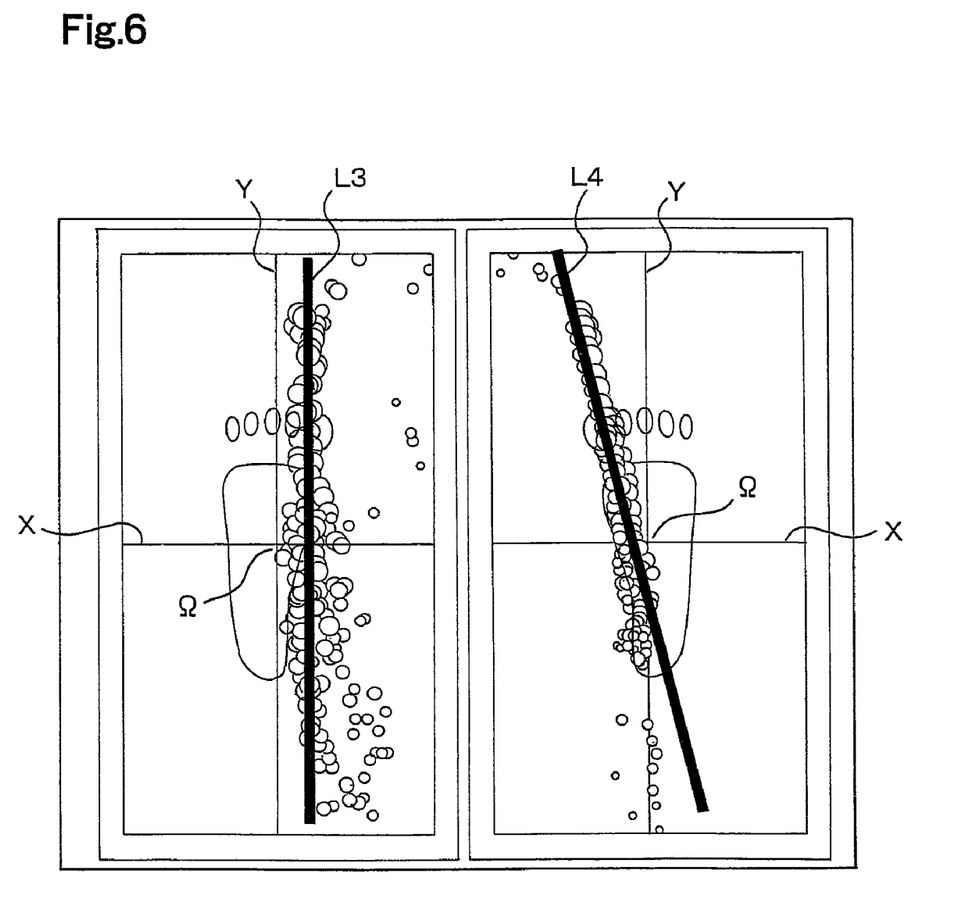
FIG. 6 illustrates a screen for showing a plane distribution of loads measured by the apparatus.

The load distribution analyzing means 37 analyzes the state of a gravity center distribution of the loads, based upon the measured values stored in the storage means 34, i.e., the values measured by each of the load sensors 7 to 12. One example of the state of the gravity center distribution of the loads obtained by the load distribution analyzing means 37 is shown in FIG. 6. In FIG. 6, each point signifies the gravity center position of the load at a given moment. That is, FIG. 6 is a view in which the gravity center positions of the loads are obtained at a pre-determined sampling interval during a pre-determined time, and these results are shown as a plurality of points. Next, a method for obtaining the state of the gravity center distribution of the loads will be described. An X-coordinate (XG) of the gravity center of the load at each moment is obtained using numerical formula 1 (below), and a Y-coordinate (YG) is obtained using numerical formula 2. The combined load F is obtained using numerical formula 3.

$$XG = (f1 - f2)a/f \quad \text{(numerical formula 1)}$$

$$YG = (f1 + f2 - f3)b/F \quad \text{(numerical formula 2)}$$

$$F = f1 + f2 + f3 \quad \text{(numerical formula 3)}$$

In the formulae shown above, and as FIG. 2 indicates, f1 is the measured value of the load sensor 7 or 10, f2 is the measured value of the load sensor 8 or 11, and f3 is the measured value of the load sensor 9 or 12. Additionally, in FIG. 6, a Y-axis is set along the axial center L1 of the footplate 5 or the axial center L2 of the footplate 6, and an X-axis is set so that it passes through a center Q of the footplate 5 or 6 and meets the Y-axis at right angles.

Next, a method will be described for making a linear approximation of the changes in the gravity center distribution of the loads, which is obtained by the load distribution analyzing means 37, over a period of time. This linear approximation is made with a least-squares method.

The linear approximation is expressed by the numerical formula 4.

$$Y = cX + d \quad \text{(numerical formula 4)}$$

The slope c and an intersection d of the straight line are derived using numerical formula 5 and numerical formula 6.

$$c = \frac{\sum_{i=1}^{n} X_i Y_i - n \langle X \rangle \langle Y \rangle}{\left( \sum_{i=1}^{n} X_i^2 - n \langle X \rangle^2 \right)} \quad \text{(numerical formula 5)}$$

In formula 5, n is the number of data points used in the calculation.

$$d = \langle Y \rangle - c \langle X \rangle \quad \text{(numerical formula 6)}$$

In this formula, $\langle X \rangle$ indicates an average coordinate of the X-coordinates at the plurality of measured load points, and $\langle Y \rangle$ indicates an average coordinate of the Y-coordinates at the plurality of measured load points. The intersection d can be obtained using the numerical formula 6. The approximate straight lines obtained in such a manner are L3 and L4 in FIG. 6. The leg strength calculating means 36 and the load distribution analyzing means 37 may be performed in software stored in the ROM 35.

Figure 7:
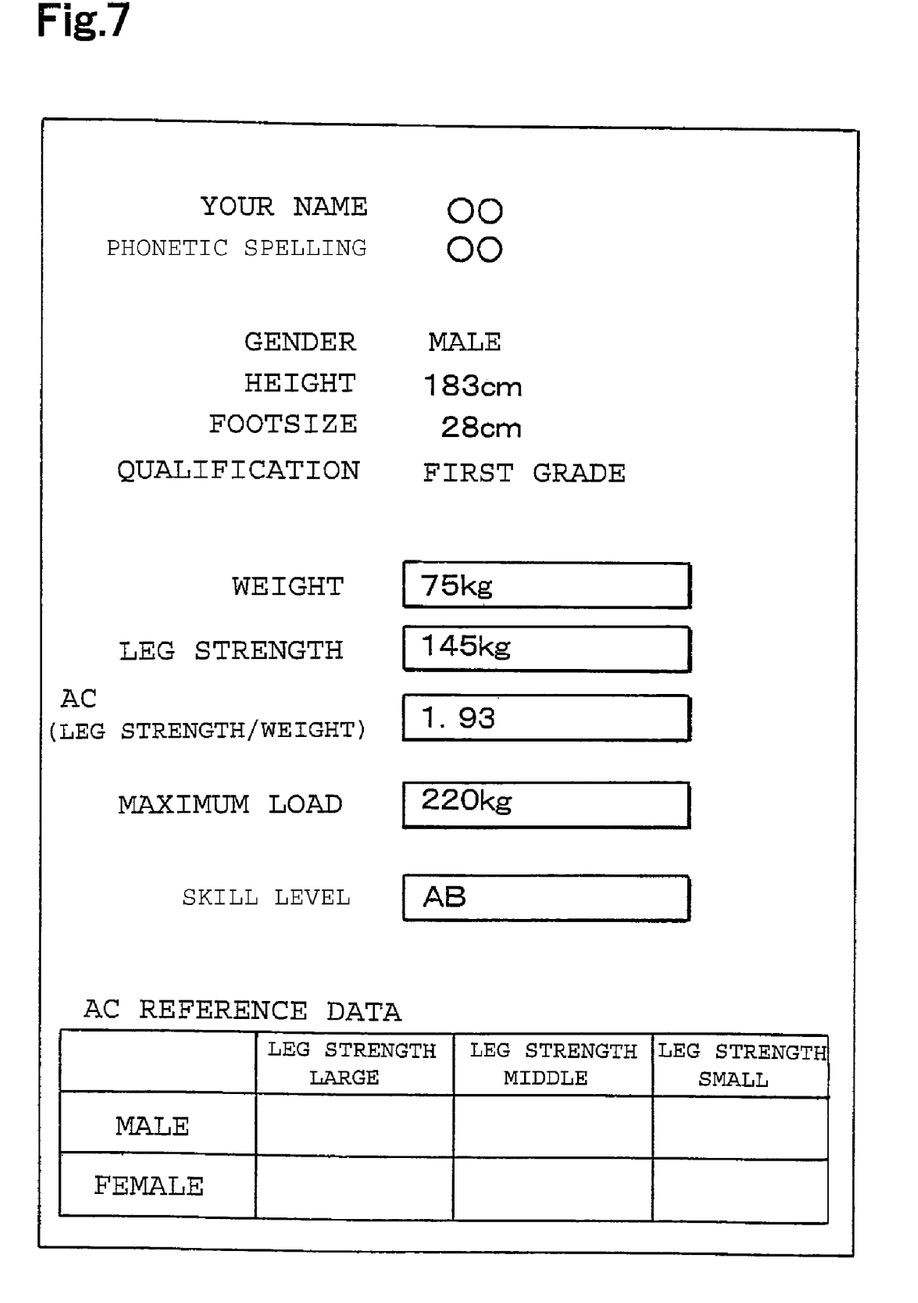
FIG. 7 is a front view of the contents of a display used in the apparatus.

The display means 32 displays the name, the weight, the leg strength, the maximum load, etc., of the person as shown in FIG. 7, and in addition displays the values measured in the load sensors 7 to 12 by a graph as shown in FIG. 5. The display means 32 also displays an image showing the distribution of the loads analyzed in the load distribution analyzing means 37 as shown in FIG. 6.

Operation of the apparatus will now be described. Referring to FIG. 1, by moving the second footplate unit 22 to towards or away from the first footplate unit 21, the gap between the footplate units 21 and 22 can be made to coincide substantially with the width of shoulders of the person, and in this state, the screws 25, 26 and 27 are tightened. This allows the position of the second footplate unit 22 to be fixed, and an appropriate spacing between the two footplate units 21 and 22 to be determined.

Next, the person opens the opener/closer 29a on the handrail 29, climbs up the step S, steps onto one footplate 5 with one leg and the other footplate 6 with the other, and straddles the two footplates 5 and 6. While so standing, the person actuates the leg strength measuring apparatus 1. Thereafter, the person makes a plurality of bending and stretching movements, flexing and extending his legs, for example, twice. At this moment, the measured values output from all load sensors 7 to 12 are stored into the storage means 34.

The leg strength calculating means 36 obtains the leg strength by subtracting the weight of the person from the maximum load measured in the measurer 2, as shown in FIG. 5.

The load distribution analyzing means 37 obtains the gravity center position at each moment by using numerical formulas 1, 2 and 3 described above, based upon the values measured in the load sensors 7 to 12. Furthermore, by continuously measuring the gravity center positions multiple times at a predetermined sampling interval, the state of the gravity center movement is obtained as shown in FIG. 6.

The display means 32 displays the name, the gender, the weight, the leg strength, the maximum load, etc. of the person as shown in FIG. 7, and in addition, graphical displays a series of the values measured in the measurer 2 as shown in FIG. 5. The display means 32 also displays the center position of the load at each moment as analyzed in the load distribution analyzing means 37 as a point, as shown in FIG. 6.

Figure 8:
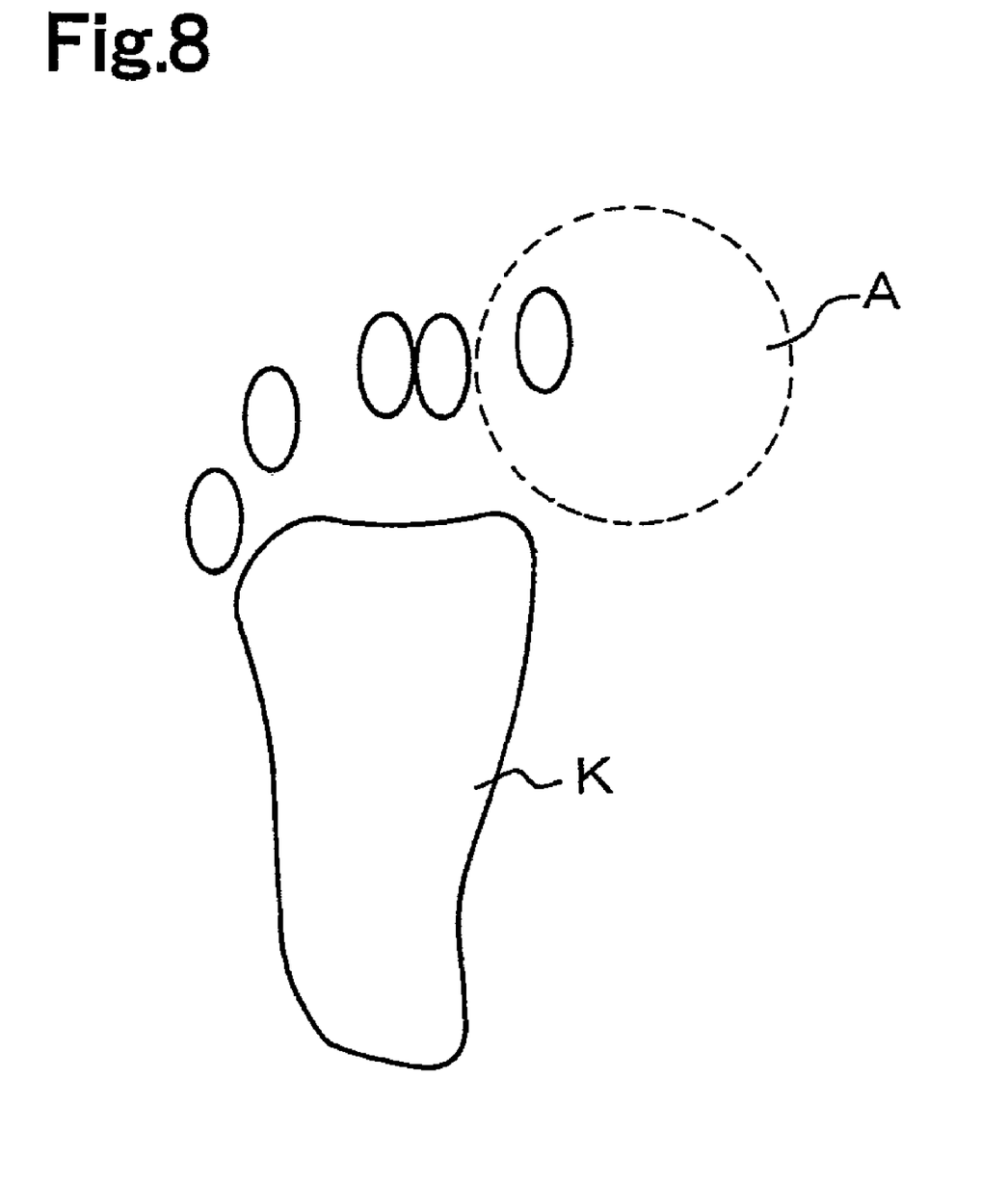
FIG. 8 is a view illustrating an ideal state of a load distribution over the sole of a foot of a user of the apparatus.

The person receives advice from a clerk of a shop selling skis, snowboards, or boots for skis or snowboards while looking at the gravity center position of the load displayed in the display means 32. In particular, in skiing or snowboarding, as shown in FIG. 8, the gravity center position of the weight of a skier or snowboarder preferably concentrates within a narrow range A on a big-toe side of the foot K. Accordingly, the person can receive from the clerk instructions for correcting his posture so that the gravity center position of the weight concentrates within a narrow range A on big-toe side of his foot.

Furthermore, by knowing the distribution of the gravity center of the person, a diagnosis or a selection of an insole suitable for each person can be made, which can be furthermore utilized for a diagnosis, a selection, and an adjustment, as well as in designing and developing boots or skis suitable for each person.

Furthermore, in general, an advanced learner among skiers or snowboarders has a tendency such that the gravity center position of the weight concentrates within the narrow range A on the foot's big-toe side as mentioned previously, and on the other hand, a beginner has a tendency wherein the gravity center position of the weight spreads across a wide range. Accordingly, the distribution of the gravity center position of the weight can be assumed as a criterion for selecting hardnesses of shells or materials for ski or snowboard boots, based upon the extent of the range of the gravity center variation. That is, it becomes possible to recommend boots having a hard shell or upper for the advanced learner and to recommend boots having a soft shell or upper for the beginner.

Additionally, providing the fitting section for fitting the ski or snowboard boots onto the footplates 5 and 6 and measuring the load while the person is wearing the ski or snowboard boots enables the person's leg strength, etc., to be measured in a situation closer to the actual use conditions. Furthermore, the person may stand and move on the footplates 5 and 6 to measure the load with the ski or snowboard boots on his feet, and in addition to that, with the ski or snowboard put on as well.

Furthermore, the footplates 5 and 6 may be provided horizontally. Placing the footplates 5 and 6 in a state inclined in a front-to-back direction or in a state inclined left and right with respect to the center in the axial centers L1 and L2 of the footplates 5 and 6 makes it possible to measure the leg strength of the person and the gravity center distribution in states that more closely reflect actually skiing or snowboarding, if the state of "tiptoe" raising or lowering, or a state of turning left and right is sought to be simulated while the person is standing on the footplates 5 and 6.

Figure 9:
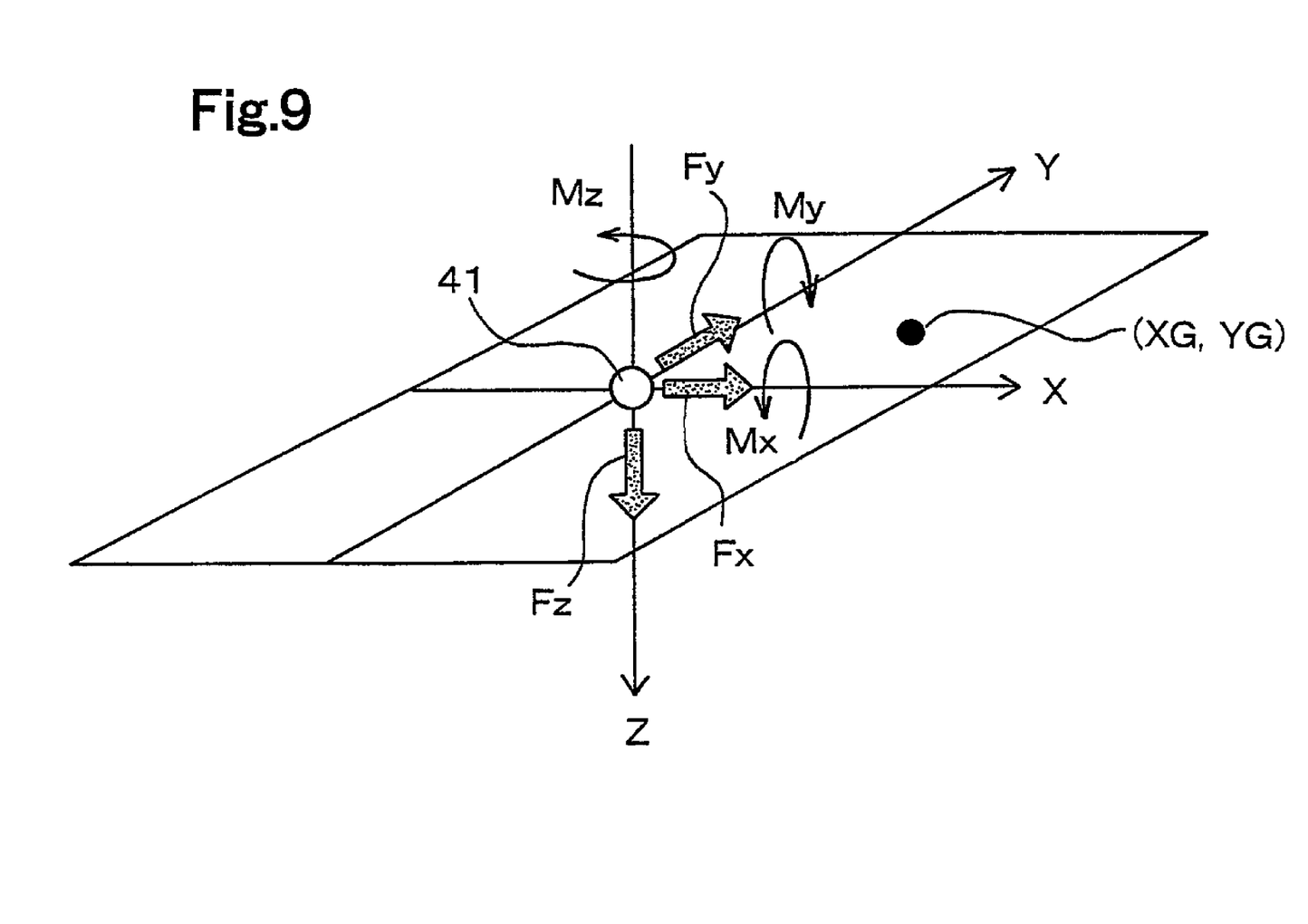
FIG. 9 is illustrating a method for obtaining measured load values employing a six-axis sensor as a load sensor.

FIG. 9 illustrates another embodiment of the invention. This embodiment employs a six-axis sensor 41 as a load sensor. In this embodiment, the planar distribution of the loads imposed by the person can be measured with one six-axis sensor 41. A method for measuring the load distribution with the six-axis sensor 41 will be described below. One six-axis sensor 41 is installed in each of the footplates 5 and 6, so the use of a six-axis sensor 41 is installed in one of the footplates 5 and 6 will now be described. First, the X-axis and the Y-axis, each of which meets the other at right angle, are set on the footplate. The X-axis or the Y-axis may be set, for example, so as to coincide with the axis center of the footplate. Next, a Z-axis that goes through an origin Ω of the X-axis and the Y-axis and that meets the X-axis and the Y-axis at right angles is set. The six-axis sensor 41 is installed in the origin Ω. The six-axis sensor 41 is a sensor capable of simultaneously measuring loads Fx, Fy and Fz parallel to the X-axis, Y-axis and Z-axis, and moments Mx, My, and Mz applied about the X-axis, the Y-axis and the Z-axis, respectively.

Each of the load values Fz, Mx, and My is measured with the person atop the footplates. This enables the load value F and the gravity center position (XG, YG) of the load to be obtained with using numerical formula 7, numerical formula 8, and numerical formula 9, as set forth below.

$F=F_z$ (numerical formula 7)

$XG=-My/F_z$ (numerical formula 8)

$YG=-Mx/F_z$ (numerical formula 9)

A linear approximation can then be made of the movement of the load point by continuing to measure the gravity center position (XG, YG) of the load at each predetermined interval. The linear approximation can be obtained with a numerical formula 10, based upon a least-squares method.

$y=cX+d$ (numerical formula 10)

The slope c and intersection d in the numerical formula 10 can be obtained using numerical formula 11 and numerical formula 12, as set forth below.

$$c = \frac{\left(\sum_{i=1}^{n} XiYi - n\langle X\rangle\langle Y\rangle\right)}{\left(\sum_{i=1}^{n} Xi^2 - n\langle X\rangle^2\right)}$$ (numerical formula 11)

In numerical formula 11, n indicates the number of data points used in the calculation.

$d=\langle Y\rangle-c\langle X\rangle$ (numerical formula 12)

In numerical formula 12, <X> indicates an average X-coordinate of the X-coordinates at each gravity center position where multiple gravity center positions are measured in sequence. Furthermore, <Y> indicates an average Y-coordinate of the Y-coordinates at each of multiple gravity center positions.

Three load sensors are provided in each of the footplates 5 and 6 in the first embodiment, with one six-axis sensor being provided in the second embodiment. The loads applied to each of the footplates 5 and 6 are measured in each embodiment. The number and kind of load sensors, though, are not limited to those used in these example embodiments, so long as the load sensor is capable of reflecting the planar distribution of the load applied to each of the footplates 5 and 6. In the first embodiment, moreover, two of the load sensors 7 and 8, and 10 and 11 are provided at the tip sides of the footplates 5 and 6 respectively, and one of the load sensors 9 and 12 is provided at the rear sides, respectively. In some cases, though, one load sensor might be provided at the tip sides of the footplates 5 and 6, respectively, with two load sensors provided at each of the rear sides.

What is claimed is:

1. Leg strength measuring apparatus comprising:
   at least one footplate configured to receive and support a person whose leg strength is to be measured as the person stands on the footplate;
   a load sensor operable to detect loads applied to the footplate;
   load comparison apparatus operable to compare a plurality of loads detected by the load sensor as the person flexes and bends at the person's knees while the person is standing on the footplate, wherein said load comparison apparatus is further operable to store data corresponding to a maximum detected load among the plurality of detected loads;
   weight detection apparatus operable to store data corresponding to a load detected by the load sensor when the person is standing stationary on the footplate; and
   leg strength calculation apparatus operable to calculate the person's leg strength based on a comparison of the data corresponding to the maximum detected load and the data corresponding to the stationary load, and corresponding to a subtraction of the stationary load from the maximum detected load.

2. The leg strength apparatus of claim 1, wherein said at least one footplate comprises two footplates, each said footplate being configured to receive and support each one of two feet of the person whose leg strength is to be measured.

3. The leg strength measuring apparatus of claim 2, wherein the load sensor is operable to detect loads applied to each footplate at three or more points.

4. The leg strength measuring apparatus of claim 2, wherein the load sensor is operable to detect a vertical load applied to each footplate, and a moment associated with that vertical load.

5. The leg strength measuring apparatus of claim 1, and further comprising structure configured to receive and fix in place on the footplate a boot to be worn by the person whose leg strength is to be measured, while that person is standing on the footplate.

6. The leg strength measuring apparatus of claim 1, and further comprising structure configured to receive and fix in place on the footplate an item selected from the group consisting of a ski and a snowboard, while the person whose leg strength is to be measured is standing on the item on the footplate.

7. The leg strength measuring apparatus of claim 1, and further comprising structure operable to fix the footplate in a position inclined in at least one of a front-to-back and a transverse direction.

* * * * *